(12) United States Patent
Pepper

(10) Patent No.: US 8,814,899 B2
(45) Date of Patent: Aug. 26, 2014

(54) BALLOON CATHETER PRESSURE RELIEF VALVE

(75) Inventor: Lanny R. Pepper, Larue, TX (US)

(73) Assignee: FutureMatrix Interventional, Inc., Athens, TX (US)

(*) Notice: Subject to any disclaimer, the term of this patent is extended or adjusted under 35 U.S.C. 154(b) by 1546 days.

(21) Appl. No.: 12/390,573

(22) Filed: Feb. 23, 2009

(65) Prior Publication Data

US 2010/0217189 A1    Aug. 26, 2010

(51) Int. Cl.
*A61M 29/00* (2006.01)

(52) U.S. Cl.
USPC ..... 606/194; 606/191; 604/96.01; 604/97.01; 604/99.01; 604/99.02; 604/99.04; 604/237

(58) Field of Classification Search
USPC ......... 606/191, 194; 604/96.01, 97.01, 99.01, 604/99.02, 99.04, 137; 251/61, 61.1; 137/14, 68.19, 68.23
See application file for complete search history.

(56) References Cited

U.S. PATENT DOCUMENTS

| 1,596,284 | A | 8/1926 | Malmgren |
| 2,043,083 | A | 6/1936 | Wappler |
| 3,769,981 | A | 11/1973 | McWhorter |
| 3,981,415 | A | 9/1976 | Fowler et al. |
| 4,367,396 | A | 1/1983 | Ravinsky |
| 4,482,516 | A | 11/1984 | Bowman et al. |
| 4,572,186 | A | 2/1986 | Gould et al. |
| 4,637,396 | A | 1/1987 | Cook |
| 4,652,258 | A | 3/1987 | Drach |
| 4,702,252 | A | 10/1987 | Brooks |
| 4,704,130 | A | 11/1987 | Gilding et al. |
| 4,706,670 | A | 11/1987 | Andersen et al. |
| 4,748,982 | A | 6/1988 | Horzewski et al. |
| 4,796,629 | A | 1/1989 | Grayzel |
| 4,834,755 | A | 5/1989 | Silvestrini et al. |
| 4,884,573 | A | 12/1989 | Wijay et al. |
| 4,952,357 | A | 8/1990 | Euteneuer |
| 4,983,167 | A | 1/1991 | Sahota |
| 4,998,421 | A | 3/1991 | Zafiroglu |
| 5,042,985 | A | 8/1991 | Elliott et al. |
| 5,046,497 | A | 9/1991 | Millar |
| 5,061,273 | A | 10/1991 | Yock |
| 5,078,727 | A | 1/1992 | Hannam et al. |
| 5,108,415 | A | 4/1992 | Pinchuk et al. |
| 5,112,304 | A | 5/1992 | Barlow et al. |
| 5,116,360 | A | 5/1992 | Pinchuk et al. |
| 5,171,297 | A | 12/1992 | Barlow et al. |

(Continued)

OTHER PUBLICATIONS

Nylon; Wikipedia, the free encyclopedia; Jun. 27, 2008; pp. 1-7; available at http://en.wikipedia.org/wiki/Nylon.
Fiber; Wikipedia, the free encyclopedia; Jun. 27, 2008; pp. 1-3; available at http://en.wikipedia.org/wiki/Fiber.

(Continued)

*Primary Examiner* — Victor Nguyen
*Assistant Examiner* — Kevin Everage
(74) *Attorney, Agent, or Firm* — Howison & Arnott, L.L.P.

(57) ABSTRACT

A pressure relief apparatus for a balloon dilation catheter having a shaft with a dilation balloon attached to the distal end of the shaft and an inflation/deflation lumen for inflating and deflating the balloon includes a pressure relief port formed through the wall of the inflation/deflation lumen with a pressure relief member secured across the pressure relief port to form a fluid tight seal such that the fluid tight seal formed by the pressure relief member fails at a predetermined pressure to release pressure from the inflation/deflation lumen through the pressure relief port.

19 Claims, 3 Drawing Sheets

(56) References Cited

U.S. PATENT DOCUMENTS

| | | |
|---|---|---|
| 5,201,706 A | 4/1993 | Noguchi et al. |
| 5,207,700 A | 5/1993 | Euteneuer |
| 5,264,260 A | 11/1993 | Saab |
| 5,270,086 A | 12/1993 | Hamlin |
| 5,290,306 A | 3/1994 | Trotta et al. |
| 5,295,960 A | 3/1994 | Aliahmad et al. |
| 5,304,340 A | 4/1994 | Downey |
| 5,306,245 A | 4/1994 | Heaven |
| 5,306,246 A | 4/1994 | Sahatjian et al. |
| 5,314,443 A | 5/1994 | Rudnick |
| 5,330,429 A | 7/1994 | Noguchi et al. |
| 5,338,299 A | 8/1994 | Barlow |
| 5,344,401 A | 9/1994 | Radisch et al. |
| 5,358,486 A | 10/1994 | Saab |
| 5,410,797 A | 5/1995 | Steinke et al. |
| 5,451,209 A | 9/1995 | Ainsworth et al. |
| 5,451,233 A | 9/1995 | Yock |
| 5,464,394 A | 11/1995 | Miller et al. |
| 5,470,314 A | 11/1995 | Wallinsky |
| 5,477,886 A | 12/1995 | Van Beugen et al. |
| 5,478,320 A | 12/1995 | Trotta |
| 5,492,532 A | 2/1996 | Ryan et al. |
| 5,549,552 A | 8/1996 | Peters et al. |
| 5,549,556 A | 8/1996 | Ndondo-Lay et al. |
| 5,554,120 A | 9/1996 | Chen et al. |
| 5,575,771 A | 11/1996 | Walinsky |
| 5,587,125 A | 12/1996 | Roychowdhury |
| 5,599,576 A | 2/1997 | Opolski |
| 5,599,578 A | 2/1997 | Opolski |
| 5,620,649 A | 4/1997 | Trotta |
| 5,647,848 A | 7/1997 | Jorgensen |
| 5,690,642 A | 11/1997 | Osborne et al. |
| 5,728,063 A | 3/1998 | Preissman et al. |
| 5,728,083 A | 3/1998 | Pressman et al. |
| 5,741,325 A | 4/1998 | Chaikof et al. |
| 5,752,934 A | 5/1998 | Campbell et al. |
| 5,755,690 A | 5/1998 | Saab |
| 5,759,172 A | 6/1998 | Weber et al. |
| 5,769,817 A | 6/1998 | Burgmeier |
| 5,772,681 A | 6/1998 | Leoni |
| 5,788,979 A | 8/1998 | Alt et al. |
| 5,797,877 A | 8/1998 | Hamilton et al. |
| 5,820,613 A | 10/1998 | Van Werven-Fransesen et al. |
| 5,868,779 A | 2/1999 | Ruiz |
| 5,879,369 A | 3/1999 | Ishida |
| 5,928,181 A | 7/1999 | Coleman et al. |
| 5,972,441 A | 10/1999 | Campbell et al. |
| 5,980,486 A | 11/1999 | Enger |
| 6,007,544 A | 12/1999 | Kim |
| 6,010,480 A | 1/2000 | Abele et al. |
| 6,012,457 A | 1/2000 | Lesh |
| 6,015,430 A | 1/2000 | Wall |
| 6,024,740 A | 2/2000 | Lesh et al. |
| 6,024,772 A | 2/2000 | Rau et al. |
| 6,027,779 A | 2/2000 | Campbell et al. |
| 6,036,697 A | 3/2000 | DiCaprio |
| 6,036,715 A | 3/2000 | Yock |
| 6,117,101 A | 9/2000 | Diederich et al. |
| 6,124,007 A | 9/2000 | Wang et al. |
| 6,127,597 A | 10/2000 | Beyar et al. |
| 6,129,708 A | 10/2000 | Enger |
| 6,156,254 A | 12/2000 | Andrews et al. |
| 6,159,238 A | 12/2000 | Killion et al. |
| 6,164,283 A | 12/2000 | Lesh |
| 6,171,297 B1 | 1/2001 | Pedersen et al. |
| 6,183,492 B1 | 2/2001 | Hart et al. |
| 6,186,978 B1 | 2/2001 | Samson et al. |
| 6,187,013 B1 | 2/2001 | Stollze et al. |
| 6,188,978 B1 | 2/2001 | Samson et al. |
| 6,213,995 B1 | 4/2001 | Steen et al. |
| 6,234,995 B1 | 5/2001 | Peacock, III |
| 6,245,064 B1 | 6/2001 | Lesh et al. |
| 6,254,599 B1 | 7/2001 | Lesh et al. |
| 6,263,236 B1 | 7/2001 | Kasinkas et al. |
| 6,270,902 B1 | 8/2001 | Tedeschi et al. |
| 6,290,485 B1 | 9/2001 | Wang |
| 6,305,378 B1 | 10/2001 | Lesh |
| 6,306,154 B1 | 10/2001 | Hudson et al. |
| 6,309,379 B1 | 10/2001 | Willard et al. |
| 6,315,751 B1 | 11/2001 | Cosgrove et al. |
| 6,328,925 B1 | 12/2001 | Wang et al. |
| 6,361,529 B1 | 3/2002 | Goodin et al. |
| 6,394,995 B1 | 5/2002 | Solar et al. |
| 6,544,219 B2 | 4/2003 | Happ et al. |
| 6,626,889 B1 | 9/2003 | Simpson et al. |
| 6,663,648 B1 | 12/2003 | Trotta |
| 6,702,750 B2 | 3/2004 | Yock |
| 6,702,782 B2 | 3/2004 | Miller et al. |
| 6,706,051 B2 | 3/2004 | Hudson et al. |
| 6,733,487 B2 | 5/2004 | Keith et al. |
| 6,743,196 B2 | 6/2004 | Barbut et al. |
| 6,746,425 B1 | 6/2004 | Beckham |
| 6,748,425 B1 | 6/2004 | Beckham |
| 6,755,845 B2 | 6/2004 | Kieturakis et al. |
| 6,761,708 B1 | 7/2004 | Chiu et al. |
| 6,899,713 B2 | 5/2005 | Shaolian et al. |
| 6,905,743 B1 | 6/2005 | Chen et al. |
| 6,911,038 B2 | 6/2005 | Mertens et al. |
| 6,942,680 B2 | 9/2005 | Grayzel et al. |
| 6,977,103 B2 | 12/2005 | Chen et al. |
| 7,252,650 B1 | 8/2007 | Andrews et al. |
| 7,300,415 B2 | 11/2007 | McMurtry et al. |
| 7,309,324 B2 | 12/2007 | Hayes et al. |
| 7,354,419 B2 | 4/2008 | Davies et al. |
| 7,435,254 B2 | 10/2008 | Chouinard et al. |
| 7,500,982 B2 | 3/2009 | Pepper |
| 7,544,201 B2 | 6/2009 | Pepper |
| 7,635,510 B2 | 12/2009 | Horn et al. |
| 7,662,163 B2 | 2/2010 | Grayzel et al. |
| 7,682,335 B2 | 3/2010 | Pepper et al. |
| 2002/0058960 A1 | 5/2002 | Hudson et al. |
| 2002/0077653 A1 | 6/2002 | Hudson et al. |
| 2002/0161388 A1 | 10/2002 | Samuels et al. |
| 2004/0015182 A1 | 1/2004 | Kieturakis et al. |
| 2004/0039332 A1 | 2/2004 | Kantor |
| 2004/0073163 A1 | 4/2004 | Tomaschko et al. |
| 2004/0073299 A1 | 4/2004 | Hudson et al. |
| 2004/0082965 A1 | 4/2004 | Beckham |
| 2004/0109964 A1 | 6/2004 | Beckham |
| 2004/0176740 A1 | 9/2004 | Chouinard |
| 2005/0027249 A1 | 2/2005 | Reifart et al. |
| 2005/0033225 A1 | 2/2005 | Wu et al. |
| 2005/0102020 A1 | 5/2005 | Grayzel et al. |
| 2005/0121073 A1* | 6/2005 | Carroll ...................... 137/68.23 |
| 2005/0123702 A1 | 6/2005 | Beckham |
| 2005/0267408 A1 | 12/2005 | Grandt et al. |
| 2005/0271844 A1 | 12/2005 | Mapes et al. |
| 2006/0015133 A1 | 1/2006 | Grayzel et al. |
| 2006/0085022 A1 | 4/2006 | Hayes et al. |
| 2006/0085023 A1 | 4/2006 | Davies et al. |
| 2006/0085024 A1 | 4/2006 | Pepper et al. |
| 2007/0010847 A1 | 1/2007 | Pepper |
| 2007/0016133 A1 | 1/2007 | Pepper |
| 2007/0059466 A1 | 3/2007 | Beckham |
| 2007/0093865 A1 | 4/2007 | Beckham |
| 2007/0213760 A1 | 9/2007 | Hayes et al. |
| 2007/0219401 A1 | 9/2007 | Pepper et al. |
| 2008/0009793 A1* | 1/2008 | Dabbs ........................ 604/99.04 |
| 2008/0082050 A1 | 4/2008 | Solar et al. |
| 2008/0183132 A1 | 7/2008 | Davies et al. |
| 2008/0188805 A1 | 8/2008 | Davies et al. |
| 2009/0043254 A1 | 2/2009 | Pepper et al. |
| 2009/0082778 A1* | 3/2009 | Beane et al. .................. 606/108 |
| 2009/0171277 A1 | 7/2009 | Pepper |
| 2009/0247947 A1 | 10/2009 | Pepper |
| 2009/0294031 A1 | 12/2009 | Pepper et al. |
| 2010/0179581 A1 | 7/2010 | Beckham |

OTHER PUBLICATIONS

Putnam Plastics Corporation; Putnam Plastics—Thermoset Polyimide Tubing; Mar. 20, 2005; available at www.putnamplastics.com.

Arkema Group; Pebax® Application Areas; Jun. 2000.

* cited by examiner

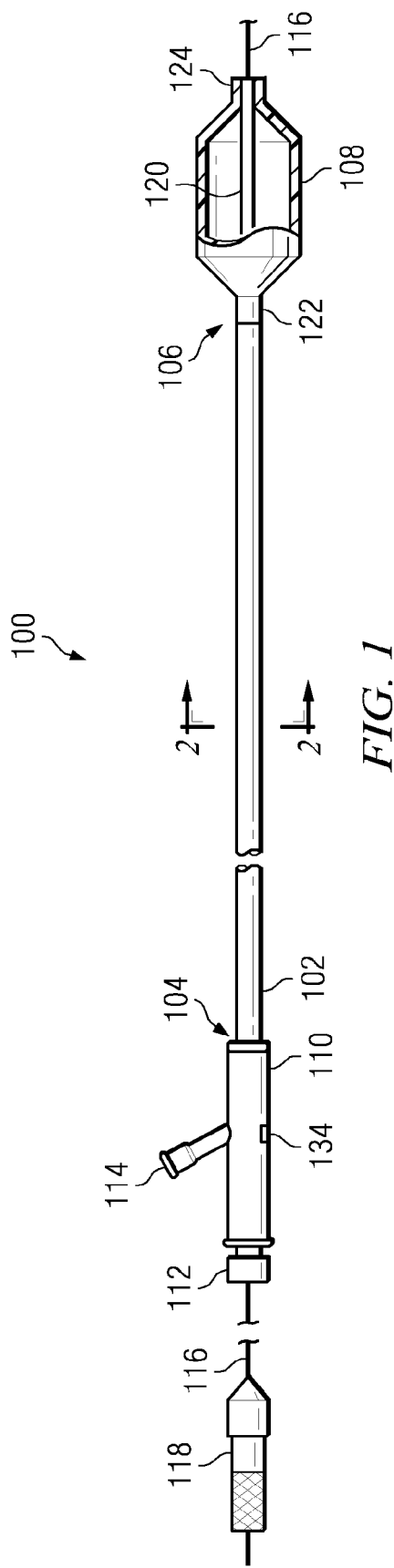
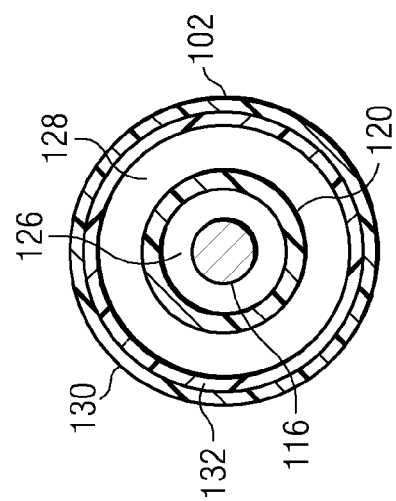

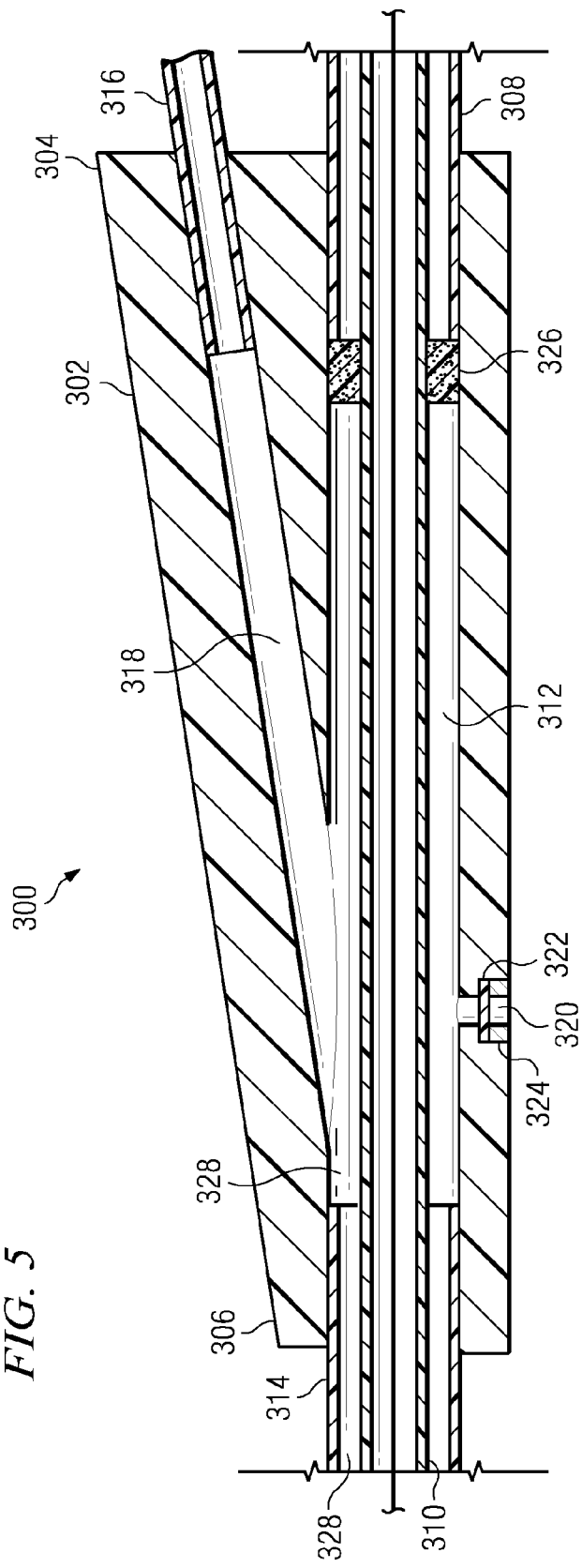
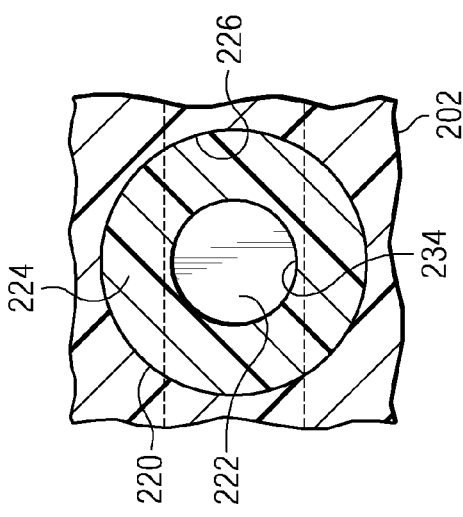

BALLOON CATHETER PRESSURE RELIEF VALVE

TECHNICAL FIELD

The disclosure relates to dilation balloon catheters and, in particular, dilation balloon catheters having a pressure relief valve for limiting the amount of pressure that may be applied to the balloon.

BACKGROUND

Angioplasty is the technique of mechanical widening a narrowed or totally obstructed blood vessel; typically as a result of atherosclerosis. A catheter is used to maneuver a tightly folded balloon attached to the distal end of the catheter into the narrowed location (stenosis). An incompressible fluid is then pumped through the catheter to inflate the balloon and enlarge the narrowed portion of the blood vessel. Relatively high pressures, in some instances up to 30 atmospheres, may be used to inflate the balloon. After the procedure is complete, a negative pressure may be applied through the catheter to remove the incompressible fluid, deflating the balloon for removal from the blood vessel.

Catheter dilation balloons are typically provided with a rated operating pressure and a rated burst pressure. The rated operating pressure is the pressure at which the balloon reaches its nominal diameter. The rated burst pressure is a statistical measure, e.g., typically a maximum pressure at which there is a 95% confidence level that 99.99% of balloons will not fail. Non-compliant catheter balloons are typically used at pressures between the rated operating pressure and the rated burst pressure.

However, due to the high pressures used in many cases to inflate a dilation catheter balloon during angioplasty and the relatively small volume of the balloons used, there is a potential to pressurize a dilation balloon beyond its rated burst pressure. Further, in some instances a dilation catheter balloon may be inflated and deflated multiple times during angioplasty, weakening the balloon. If a balloon bursts during angioplasty, there is a possibility that portions of the balloon may separate from the catheter, possibly necessitating surgery to remove the separated portions of the balloon from the patient's artery. Thus, there exists a need for a means of preventing over-inflation of dilation balloons during procedures such as angioplasty.

SUMMARY

In one aspect thereof, a pressure relief apparatus for a balloon dilation catheter is provided. The balloon dilation catheter includes a shaft having a dilation balloon attached to the distal end of the shaft, an inflation/deflation lumen for inflating and deflating the balloon and a pressure relief port formed through the wall of the inflation/deflation lumen. A pressure relief member is secured across the pressure relief port to form a fluid tight seal. The fluid tight seal is configured to fail (e.g. burst, rupture, tear or leak) at a predetermined pressure to release pressure from the inflation/deflation lumen through the pressure relief port. The predetermined pressure may be greater than or equal to the rated burst pressure of the dilation balloon.

In one variation, the pressure relief port comprises a first outwardly opening passage and a second passage in fluid communication with the first passage. The second passage extends inwardly from the first passage and opens into the inflation/deflation lumen. In this variation, the cross-sectional area of the first passage may be larger than the cross-sectional area of the second passage.

In one embodiment, a wall extends radially between an inside end of the first passage of the pressure relief port and an outside end of the second passage of the pressure relief port. The pressure relief member may be disposed adjacent the wall and across the outside end of the second passage of the pressure relief port to block the pressure relief port and form a fluid tight seal. The pressure relief member may be a plastic film, a thin metallic film or a similar material. A retainer for retaining the pressure relief member in the pressure relief port may be utilized such that the pressure relief member and retainer form a fluid tight seal across the pressure relief port.

In another aspect, a pressure relief apparatus for a dilation catheter having a balloon with a rated burst pressure includes a hub adapted for connection to a proximal end portion of a balloon dilation catheter shaft wherein a pressure relief port is formed in the hub. In one embodiment, the hub may comprise a plastic a body that defines an inflation/deflation lumen and a guidewire lumen.

The hub may be formed from a substantially rigid material and includes a wall defining the inflation/deflation lumen for directing a substantially incompressible inflation medium into and from an inflation/deflation lumen of the catheter shaft. The hub includes a pressure relief port formed through the wall of the hub and a pressure relief member disposed across the pressure relief port to form a fluid tight seal across the pressure relief port. The pressure relief member is configured to fail, (e.g. rupture, tear, burst or leak), at a predetermined pressure to release pressure from the inflation/deflation port through the pressure relief port.

In one configuration the relief port includes a first outwardly opening passage and a second passage in fluid communication with the first passage. The second passage extends inwardly from the first passage and opens into the inflation lumen of the hub. A wall extends radially between an inside end of the first passage of the pressure relief port and an outside end of the second passage of the pressure relief port. In this variation, the pressure relief member may be disposed adjacent the wall and across the outermost end of the second passage of the pressure relief port. The pressure relief member may be secured against the wall and across the outside end of the second passage with a retainer positioned in the first passage whereby the pressure relief member and retainer form a fluid tight seal across the pressure relief port.

In another aspect, a dilation catheter having a pressure relief apparatus includes a catheter shaft having a proximal end portion and a distal end portion with a dilation balloon having a rated burst pressure attached to the distal end portion of the catheter shaft. The catheter shaft includes an outer tubular member that forms an inflation/deflation lumen extending through the catheter shaft from adjacent the proximal end portion of the catheter shaft to the balloon such that the inflation/deflation lumen is in fluid communication with the balloon. A hub is connected to the proximal end portion of the catheter shaft. The hub may be formed from a substantially rigid material and has a wall defining an inflation/deflation lumen for directing a substantially incompressible inflation medium into and from the inflation/deflation lumen of the catheter shaft.

In one variation, the pressure relief apparatus includes a pressure relief port is formed through the wall of the hub. The pressure relief port may include a first outwardly opening passage and a second passage in fluid communication with the first passage and extending inwardly from the first passage and opening into the inflation/deflation lumen. In one embodiment, the diameter and cross-sectional area of the first passage is larger than the diameter and cross-sectional area of the second passage. A pressure relief member may be disposed adjacent an annular wall that extends between an inside end of the first passage of the pressure relief port and an outside end of the second passage of the pressure relief port. The pressure relief member blocks the pressure relief port, forming a fluid tight seal at pressures less than the rated burst pressure of the balloon. A retainer positioned in the first passage may be utilized to retain the pressure relief member against the annular wall. In one variation, the pressure relief member is one or more layers of a plastic film, in other variations the pressure relief member may be a thin layer of metallic material.

BRIEF DESCRIPTION OF THE DRAWINGS

For a more complete understanding, reference is now made to the following description taken in conjunction with the accompanying Drawings in which:

FIG. 1 illustrates a balloon dilation catheter according to the disclosure;

FIG. 2 is cross-sectional of the shaft of the catheter of FIG. 1, taken along line 2-2 of FIG. 1;

FIG. 5 is an end view of the pressure relief port of FIG. 4; and

FIG. 6 is a length-wise section view of an alternate hub for use with a balloon dilation catheter.

DETAILED DESCRIPTION

Figure 4:
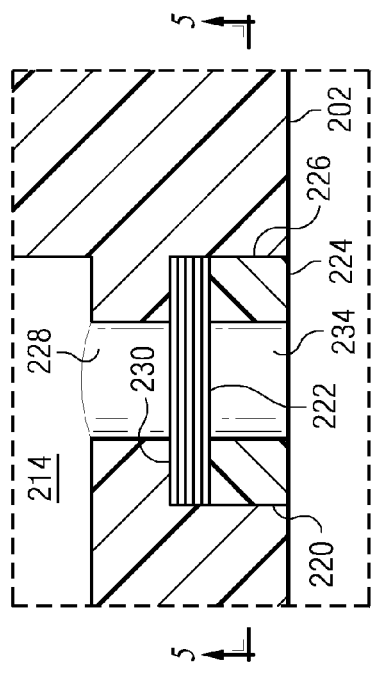
FIG. 4 is an enlarged view of a portion of the sectional view of FIG. 3 further illustrating the pressure relief port.

Referring now to the drawings, wherein like reference numbers are used herein to designate like elements throughout, the various views and embodiments of a balloon catheter pressure relief valve are illustrated and described, and other possible embodiments are described. The figures are not necessarily drawn to scale, and in some instances the drawings have been exaggerated and/or simplified in places for illustrative purposes only. One of ordinary skill in the art will appreciate the many possible applications and variations based on the following examples of possible embodiments.

Turning now to FIG. 1 a balloon dilation catheter 100 includes a shaft 102 having a proximate end 104 and a distal end 106. In one variation, a plurality of tubular members disposed in catheter 100 define internal, longitudinally extending passages known as lumens. An access fitting or hub 110 is affixed to the proximal end of catheter shaft 102 to provide access to the lumens. One tubular member, the guidewire tubular member 120, extends longitudinally through the catheter from hub 110 to the distal end 124 of dilation balloon 108. The guidewire tubular member 120 has a bore defining a guidewire lumen through which a conventional guidewire 116 may be directed through the interior of catheter 100.

As illustrated, hub 110 includes a first port 112 for receiving guidewire 116 therethrough and directing the guidewire into the guidewire lumen in shaft 102. Hub 110 further includes a second inflation/deflation port 114 adapted to receive an incompressible inflation medium and direct the medium into an inflation/deflation lumen that extends through the hub and shaft 102. As illustrated, hub 110 includes a pressure relief port 134 that extends through the wall of the hub and into the inflation/deflation lumen of the hub. A manipulator 118 may be provided for rotating and positioning guidewire 116 from the proximal end of catheter 100.

Referring still to FIG. 1, the proximal end 122 of dilation balloon 108 is affixed to the distal end 106 of shaft 102. In the case of non-compliant balloons typically used in angioplasty, balloon 108 may be of conventional construction and is typically formed of relatively non-distensible plastic or polymer material such as nylon. Non-compliant balloons will typically expand less than about 10%, and more typically less than about 5%, when pressurized from the rated operating pressure to the balloon's rated burst pressure.

The envelope of balloon 108 may be plain or reinforced with filaments or fibers. For the purpose of illustration, balloon 108 is shown in an inflated configuration in FIG. 1 with portions of the balloon cut away to better to illustrate the interior structure of catheter 100. Although balloon 108 is illustrated in an inflated configuration, it will be appreciated that when deflated the balloon can typically be folded in such a manner as to have an outside diameter or cross section approximately equal to that of catheter shaft 102.

The proximate end 122 of balloon 108 may be attached to the distal end 106 of shaft 102 of shaft 102 using various techniques known in the art, for example with an appropriate adhesive such as medical grade epoxy adhesive. The distal end 124 of balloon 108 is connected with a fluid-tight seal to the outside (i.e. radial) surface of guidewire tubular member 120, which, as illustrated, extends beyond the distal end 106 of the catheter shaft 102, passing through the interior of balloon 108. The distal end 124 of balloon 108 may be welded to guidewire tubular member 120 or adhered to the guidewire tubular member with an appropriate adhesive to form a fluid-tight seal.

FIG. 2 is a cross-sectional view of catheter shaft 102 taken along line 2-2 of FIG. 1. In one embodiment, catheter shaft 102 may have a coaxial configuration wherein guidewire tubular member 120 defines a guidewire lumen 126. An outer tubular member 132 extends coaxially with guidewire lumen 126 and defines an annular inflation/deflation lumen 128 between the inside surface of the outer tubular member and the outside surface of guidewire tubular member 120. Inflation/deflation lumen 128 extends from inflation/deflation port 114 of hub 110 to balloon 108, providing a fluid passageway for the incompressible fluid used to inflate the balloon. Catheter shaft 102 may include a coating 130 to increase the lubricity of the catheter shaft.

Outer tubular member 132 and guidewire tubular member 120 may be formed from a variety of suitable plastic materials such as nylon-11, nylon-12 and/or a polyether block amide (PEBA). In one embodiment, guidewire tubular member 120 and/or outer tubular member 132 may be formed from PEBA elastomers sold under the trademark Pebax®. PEBA elastomers are available in plasticizer and additive-free medical grades having a nominal hardness (Shore D) from about Shore D 30 to about Shore D 72. The thermoplastic materials used to make guidewire tubular member 120 and outer tubular member 132 may be loaded with materials such as carbon nanotubes or similar materials in order to enhance the strength of the tubular members. In other variations, guidewire tubular member 120 and/or outer tubular member 132 may be loaded with up to approximately twenty percent by weight of a radiopaque material such as bismuth.

Figure 3:
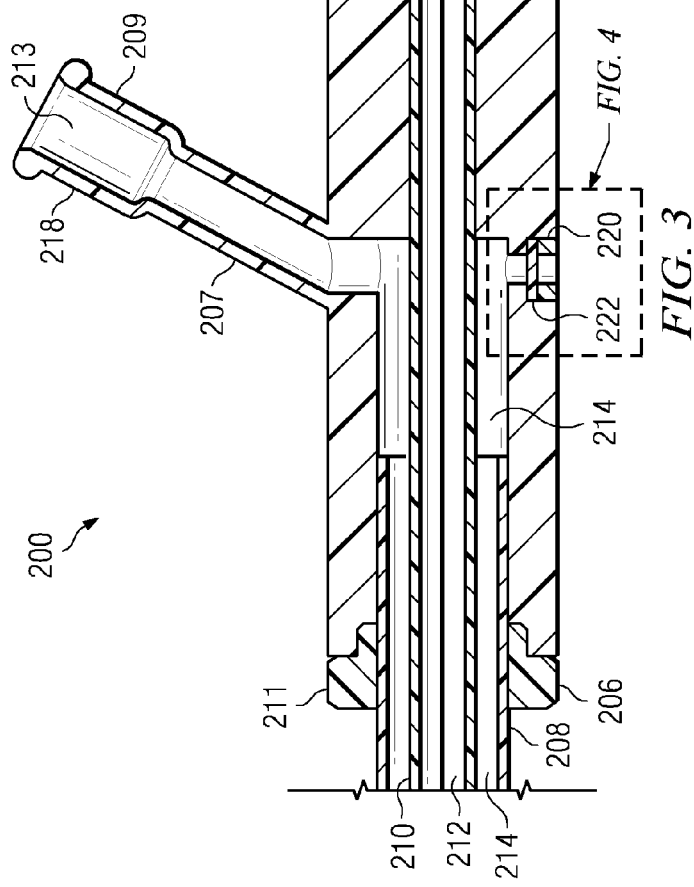
FIG. 3 is a length-wise section view of the hub of the balloon dilation catheter of FIG. 1.

FIG. 3 is a length wise sectional view of a hub 200 according to the disclosure. Hub 200 may be molded from an appropriate plastic such as nylon and includes a substantially rigid cylindrical wall 202 having a proximate end 204 and a distal end 206. In one embodiment hub 200 may include a separately molded end cap 211 that is glued into the distal end of the hub with an appropriate adhesive to facilitate assembly of the hub.

Cylindrical wall 202 defines a central passage 205 extending longitudinally through hub 200. An outer tubular member 208 of a catheter shaft may be inserted into the distal end of the passage 205 and secured to an inside surface of cylindrical wall 202 with an adhesive such as a medical grade epoxy to provide a fluid tight seal. A guidewire tubular member 210 is positioned inside outer tubular member 208. Guidewire tubular member 210 extends past the proximate end of the outer tubular member 208 and may be secured to the inside surface of cylindrical wall 202 with an appropriate adhesive to form a fluid tight seal. Guidewire tubular member 208 and the inside surface of cylindrical wall 202 proximate to the end of guidewire tubular member define a guidewire lumen 212 extending through hub 200. In one variation, an enlarged portion 216 of the proximate end of passage 205 serves as a guide for inserting or threading guidewire 232 into hub 200.

The inside surface of wall 202 (i.e., proximate to the end of the outer tubular member 208) and the outside surface of guidewire tubular member 210 define an annular inflation/deflation lumen 214 within hub 200 that extends distally from the location where guidewire tubular member 210 is sealed against the inside surface of wall 202. Inflation/deflation lumen 214 extends from hub 200 between the inside surface of the outer tubular member 208 and the outside surface of guidewire tubular member 210 to a dilation balloon such as balloon 108 of FIG. 1. Hub 200 includes an inflation/deflation port 218 through which an incompressible fluid (e.g. inflation medium) may be directed into and out of the hub. In one variation, inflation/deflation port 218 comprises a cylindrical wall 207 that may be integrally molded with wall 202. As illustrated, wall 207 defines a passageway 213 that opens into inflation/deflation lumen 214 at a location distal to the fluid tight seal between guidewire tubular member 210 and the inside surface of cylindrical wall 202. In the illustrated embodiment, cylindrical wall 207 includes an enlarged end 209 to facilitate connection of a source of pressurized fluid to hub 200.

Referring still to FIG. 3, a pressure relief port 220 is formed through cylindrical wall 202. Pressure relief port 220 opens into inflation/deflation lumen 214 and a pressure relief member 222 is secured across the pressure relief port to form a fluid tight seal. In one embodiment, pressure relief member 222 may be one or more layers of a suitable plastic film having a tensile strength such that film ruptures or tears when the pressure in inflation/deflation lumen 214 exceeds a predetermined value, for example a selected pressure between 6 and 30 atmospheres. The predetermined pressure value may be approximately equal to the rated burst pressure of a dilation balloon used with a catheter incorporating hub 200. In other variations, the predetermined value may be greater than or less than the rated burst pressure of the balloon.

FIG. 4 is an enlarged view of the indicated portion of FIG. 3 further illustrating relief port 220. As illustrated, relief port 220 includes an enlarged outwardly opening passage 226 and a smaller diameter inner passage 228 that opens into inflation/deflation lumen 214. An annular wall 230 extends radially between outwardly opening passage 226 and inner passage 228. As illustrated, pressure relief member 222 extends across inner passage 228 and annular wall 230. Pressure relief member 222 may be glued to annular wall 230 with an appropriate adhesive, such as a medical grade epoxy, to form a fluid-tight seal across relief port 220. In other embodiments, pressure relief member 222 may be solvent welded or thermally or ultrasonically welded in place. In one embodiment, a cylindrical retainer 224 is positioned in outwardly opening passage 226 over pressure relief member 222. In the embodiment shown in FIG. 4, pressure relief member 222 is positioned between retainer 224 and annular wall 230.

FIG. 5 is an enlarged end view of relief port 220. As illustrated, retainer 224 has an outside diameter approximately equal to the inside diameter of outwardly opening passage 226 and a centrally located cylindrical opening 234 having a diameter approximately equal to the diameter of inner passage 228 through which pressure relief member 222 is exposed. Retainer 224 may be secured in outwardly opening passage 226 and/or to pressure relief member 222 with an appropriate adhesive or by means of solvent, thermal or ultrasonic welding.

In the illustrated embodiments, relief port 220 has a generally circular configuration. However, in other embodiments relief port 220 may be rectangular, oval or polygonal. In other variations relief member 222 and retainer 224 may be formed as a single integral component by means of, for example, molding. In yet other embodiments, pressure relief member 222 may be scored or otherwise weakened in order to burst at a selected predetermined pressure. Although as illustrated, pressure relief member 222 is formed from one or more layers of a plastic film, it is contemplated that the relief member may be formed form other materials having the same or different geometries. For example, pressure relief member may be formed as a thin metal disk having a flat or curved cross-section.

Turning to FIG. 6, in an alternate embodiment, a catheter hub 300 comprises a substantially rigid, integrally formed body 302 having a proximate end 304 and a distal end 306. Body 302 may be molded from a suitable plastic such as nylon. A guidewire tubular member 310 passes through a longitudinally extending central passage 312 formed in body 302. A proximate portion of guidewire tubular member 310 is encased in a first outer tubular member 308 that extends into the proximate end of central passage 312. First outer tubular member 308 and guidewire tubular member 310 are secured in position in hub 300 with an adhesive 326 that forms a fluid tight seal between the guidewire tubular member and the inside surface of central passage 312. A second outer tubular member 314 is positioned over guidewire tubular member 310 and secured in central passage 312 at the distal end 306 of hub 300 with an appropriate adhesive or by means of thermal, solvent or ultrasonic welding. The inner surface of central passage 312 and the outer surface of guidewire tubular member 310 define an annular inflation/deflation lumen 328 that extends from hub 300 between the outer surface of guidewire tubular member 310 and the inner surface of second outer tubular member 314.

Referring still to FIG. 6, an inflation/deflation tube 316 is secured in an inflation/deflation port 318 that is formed in body 302 for providing pressured fluid through hub 300 to a dilation balloon. Inflation/deflation tube 316 may be secured in inflation/deflation port 318 by means of an adhesive or by thermal, ultrasonic or solvent welding. As illustrated, inflation/deflation port 318 is formed at an acute angle to central passage 312 and opens into inflation deflation lumen 328 distal to the fluid tight seal formed by adhesive 326 between the inside surface of the central passage and guidewire tubular member 310.

A pressure relief port 320 formed in body 302 extends outwardly from inflation/deflation lumen 328 at a location distal to the fluid tight seal formed by adhesive 326 between the inside surface of the central passage 312 and guidewire tubular member 310. In one variation, pressure relief port 320 is essentially identical to pressure relief port 220 of FIGS. 4 and 5. A pressure relief member 322 is secured across pressure relief port 320 to form a fluid tight seal. In one embodiment, a cylindrical retainer 324 is used to secure pressure relief member 322 across pressure relief port 320. Pressure relief member 322 is formed from a material, such as a plastic film, such that the member will rupture or tear when the pressure in inflation/deflation lumen 328 reaches or exceeds a predetermined level. In one variation, the predetermined pressure is equal to or greater than the rated burst pressure of the dilation balloon connected to hub 300.

Referring to FIGS. 3 and 6 it will be appreciated that in the event that a pressure relief member 222 or 322 is ruptured or fails during angioplasty or during stent placement, balloon 108 (FIG. 1) may remain in an inflated or partially inflated condition in a patient's blood vessel. Depending upon the particular situation, it may be difficult or impossible to remove the balloon from the blood vessel without completely deflating the balloon. Further, the blood vessel may remain occluded for longer than desired if the balloon cannot be deflated with the use of negative pressure. This may be particularly problematic in the case of a substantially inelastic non-compliant or semi-compliant balloon since the balloon may not collapse or only partially collapse without the use of negative pressure to aspirate the incompressible fluid from the balloon.

Referring still to FIGS. 3 and 6, pressure relief ports 220 and 320 are located in hubs 200 and 300 at locations where the ports may be rapidly sealed in the event of a rupture of pressure relief members 222 or 322. For example, in the case of a rupture of pressure relief member 222 or 322, a practitioner may place a finger or thumb over the pressure relief port to seal the port and then apply a negative pressure to balloon through the catheter to aspirate the fluid from the balloon. Alternatively, a piece of tape or similar material may be placed over pressure relief ports 220 or 320 to seal the port while the balloon is deflated. Thus, while pressure relief ports 220 and 320, along with relief members 222 and 322 provide a means of preventing over-inflation of dilation balloons during procedures such as angioplasty, the ports may also be rapidly re-sealed to allow for rapid controlled deflation of a dilation balloon in the case of a rupture of the relief member.

While the pressure relief ports and apparatus described above are formed in a wall of a catheter hub, it is contemplated that the ports could be positioned in a wall of the catheter shaft or in an inflation/deflation port connected to the hub. Further, while the pressure relief ports are described in connection with catheters having coaxially configured catheter shafts, the ports may be adapted for use with other types of catheters. Such catheters may have non-coaxial multi-lumen shafts such as extruded dual lumen shafts. Additionally, while the pressure relief apparatus had been described in connection with non-compliant dilation balloons, the apparatus may be used with semi-compliant and complaint balloons.

It will be appreciated by those skilled in the art having the benefit of this disclosure that this balloon catheter pressure relief valve provides a means of preventing over-pressurization of a dilation catheter balloon. It should be understood that the drawings and detailed description herein are to be regarded in an illustrative rather than a restrictive manner, and are not intended to be limiting to the particular forms and examples disclosed. On the contrary, included are any further modifications, changes, rearrangements, substitutions, alternatives, design choices, and embodiments apparent to those of ordinary skill in the art, without departing from the spirit and scope hereof, as defined by the following claims. Thus, it is intended that the following claims be interpreted to embrace all such further modifications, changes, rearrangements, substitutions, alternatives, design choices, and embodiments.

What is claimed is:

1. A pressure relief apparatus for a balloon dilation catheter including a shaft having a dilation balloon attached to the distal end of the shaft and an inflation/deflation lumen for inflating and deflating the balloon comprising:
    a pressure relief port formed through the wall of the inflation/deflation lumen wherein fluid enters and leaves the inflation/deflation lumen via an inflation/deflation port, and wherein, the pressure relief port further comprises a first outwardly opening passage and a second passage in fluid communication with the first passage and extending inwardly from the first passage and opening into the inflation/deflation lumen, and wherein the cross-sectional area of the first passage is larger than the cross-sectional area of the second passage;
    a pressure relief member secured across the pressure relief port in the wall of the inflation/deflation lumen to form a fluid tight seal, enabling inflation of the dilation balloon with a substantially incompressible fluid provided through the inflation/deflation lumen; and
    wherein the fluid tight seal formed by the pressure relief member fails at a predetermined pressure to release pressure from the inflation/deflation lumen through the pressure relief port, and wherein the pressure relief member is operative to fail during inflation of the balloon when the pressure in the inflation/deflation lumen exceeds the predetermined pressure.

2. The pressure relief apparatus of claim 1 further comprising:
    a wall extending between an inside end of the first passage of the pressure relief port and an outside end of the second passage of the pressure relief port; and
    wherein the pressure relief member is disposed adjacent the wall and across the outside end of the second passage of the pressure relief port, the pressure relief member blocking the pressure relief port.

3. The pressure relief apparatus of claim 2 further comprising a retainer for retaining the pressure relief member in the pressure relief port, the pressure relief member and retainer forming a fluid tight seal across the pressure relief port.

4. The pressure relief apparatus of claim 1 further comprising a hub attached to a proximate end of the catheter shaft and wherein the pressure relief port is formed in the hub.

5. The pressure relief apparatus of claim 1 wherein the predetermined pressure is equal to or greater than the rated burst pressure of the dilation balloon.

6. The pressure relief apparatus of claim 1 wherein the pressure relief member is a plastic film.

7. A pressure relief apparatus for a balloon dilation catheter including a balloon have a rated burst pressure, the pressure relief apparatus comprising:
    a hub adapted for connection to a proximal end portion of a balloon dilation catheter shaft, the hub being formed from a substantially rigid material and defining a guidewire access passage and having a wall defining an inflation/deflation port at a first location in the hub in fluid communication with an inflation/deflation lumen for directing a substantially incompressible inflation medium into and from an inflation/deflation lumen of the catheter shaft;
    a pressure relief port formed through the wall of the hub at a second location in the hub whereby the pressure relief port is physically separate from the inflation/deflation port;

a pressure relief member disposed across the pressure relief port, the pressure relief member forming a fluid tight seal across the pressure relief port; and wherein the fluid tight seal formed by the pressure relief member fails at a predetermined pressure to release pressure from the inflation/deflation lumen through the pressure relief port.

8. The pressure relief apparatus of claim 7 wherein the pressure relief port includes a first outwardly opening passage and a second passage in fluid communication with the first passage and extending inwardly from the first passage and opening into the inflation/deflation lumen and wherein the cross-sectional area of the first passage is larger than the cross-sectional area of the second passage.

9. The pressure relief apparatus of claim 8 further comprising a wall extending radially between an inside end of the first passage of the pressure relief port and an outside end of the second passage of the pressure relief port.

10. The pressure relief apparatus of claim 9 wherein the pressure relief member is disposed adjacent the wall and across the outermost end of the second passage of the pressure relief port.

11. The pressure relief apparatus of claim 10 further comprising a retainer for retaining the pressure relief member in the pressure relief port, the pressure relief member and retainer forming a fluid tight seal across the pressure relief port.

12. The pressure relief apparatus of claim 11 wherein the pressure relief member is disposed between the retainer and the wall.

13. The pressure relief apparatus of claim 7 wherein the predetermined pressure is equal to or greater than a rated burst pressure of the dilation balloon.

14. The pressure relief apparatus of claim 7 wherein the hub comprises a body defining an inflation/deflation port and a guidewire lumen and wherein a longitudinal axis of the inflation port forms an acute angle with the guidewire lumen.

15. A balloon dilation catheter comprising:
a catheter shaft having a proximal end portion and a distal end portion;
a dilation balloon attached to the distal end portion of the catheter shaft, the dilation balloon having a rated burst pressure;
the catheter shaft further comprising an outer tubular member that forms an inflation/deflation lumen extending through the catheter shaft from adjacent the proximal end portion of the catheter shaft to the balloon, the inflation/deflation lumen in fluid communication with the balloon;
a hub connected to the proximal end portion of the catheter shaft, the hub being formed from a substantially rigid material and having a wall defining an inflation/deflation lumen for directing a substantially incompressible inflation medium into and from the inflation/deflation lumen of the catheter shaft and having a guidewire passage formed therethrough;
an inflation/deflation port in fluid communication with the inflation/deflation lumen for directing a substantially incompressible fluid into and from the inflation/deflation lumen of the hub;
a pressure relief port formed through the wall of the hub at a location physically separate from the inflation/deflation port, the pressure relief port having a first outwardly opening passage and a second passage extending inwardly from the first passage and opening into the inflation/deflation lumen and wherein the cross-sectional area of the first passage is larger than the cross-sectional area of the second passage;
a wall extending between an inside end of the first passage of the pressure relief port and an outside end of the second passage of the pressure relief port;
a pressure relief member disposed adjacent the wall and across the outermost end of the second passage of the pressure relief port, the pressure relief member blocking the pressure relief port;
a retainer for retaining the pressure relief member in the pressure relief port, the pressure relief member and retainer forming a fluid tight seal across the pressure relief port at pressures less than the rated burst pressure of the balloon; and
wherein the fluid tight seal formed by the pressure relief member enables inflation of the dilation balloon with a substantially incompressible fluid at a pressure lower than a predetermined pressure and wherein the pressure relief member fails at a predetermined pressure, relieving pressure in the dilation balloon.

16. The balloon dilation catheter of claim 15 wherein the catheter shaft further comprises a guidewire lumen for receiving a guidewire therethrough and wherein the hub further comprises a guidewire access port for directing a guidewire into the guidewire lumen.

17. The balloon dilation catheter of claim 16 wherein the first and second passages of the pressure relief port have a generally circular configuration.

18. The balloon dilation catheter of claim 15 wherein the pressure relief member comprises one or more layers of a plastic film.

19. The balloon dilation catheter of claim 18 wherein the predetermined pressure is equal to or higher than the rated burst pressure of the balloon.

* * * * *